(12) United States Patent
MacKinnon et al.

(10) Patent No.: US 7,075,636 B2
(45) Date of Patent: Jul. 11, 2006

(54) APPARATUS AND METHODS FOR EVALUATING PERFORMANCE OF ENDOSCOPY DEVICES AND SYSTEMS

(75) Inventors: Nicholas B. MacKinnon, Vancouver (CA); Ulrich Stange, Vancouver (CA)

(73) Assignee: Tidal Photonics, Inc., Vancouver (CA)

( * ) Notice: Subject to any disclaimer, the term of this patent is extended or adjusted under 35 U.S.C. 154(b) by 0 days.

(21) Appl. No.: 10/794,761

(22) Filed: Mar. 4, 2004

(65) Prior Publication Data

US 2004/0227935 A1  Nov. 18, 2004

Related U.S. Application Data

(62) Division of application No. 09/661,602, filed on Sep. 14, 2000, now Pat. No. 6,734,958.

(60) Provisional application No. 60/154,497, filed on Sep. 17, 1999.

(51) Int. Cl.
*G01J 1/04* (2006.01)

(52) U.S. Cl. .............. 356/236; 356/24.1; 356/319; 250/228

(58) Field of Classification Search ........... 356/236, 356/243.1, 243.5, 243.8, 213, 215, 218, 234, 356/319, 416, 418, 323, 73.1; 250/228; 600/103
See application file for complete search history.

(56) References Cited

U.S. PATENT DOCUMENTS

| 4,561,776 | A | * | 12/1985 | Pryor ........................ 356/72 |
|---|---|---|---|---|
| 4,867,563 | A | | 9/1989 | Wurm et al. ............... 356/328 |
| 4,915,500 | A | * | 4/1990 | Selkowitz ................... 356/221 |
| 4,932,779 | A | * | 6/1990 | Keane ........................ 356/319 |
| 5,098,195 | A | * | 3/1992 | Halyo et al. .................. 374/9 |
| 5,251,004 | A | * | 10/1993 | Doiron et al. .............. 356/236 |
| 5,272,518 | A | * | 12/1993 | Vincent ...................... 356/405 |
| 5,369,481 | A | | 11/1994 | Berg et al. .................. 356/319 |
| 5,494,530 | A | | 2/1996 | Graf ............................ 134/18 |
| 5,555,085 | A | | 9/1996 | Bogdanowicz et al. ..... 356/300 |
| 5,738,824 | A | | 4/1998 | Pfeifer ......................... 422/3 |
| 5,820,547 | A | | 10/1998 | Strobl et al. ................ 600/127 |
| 5,841,525 | A | | 11/1998 | Rosow et al. ............ 356/124.5 |
| 5,953,112 | A | * | 9/1999 | Rosow et al. .............. 356/73.1 |
| 6,369,883 | B1 | * | 4/2002 | Clark ........................ 356/73.1 |
| 6,388,742 | B1 | * | 5/2002 | Duckett ..................... 356/73.1 |
| 6,424,413 | B1 | * | 7/2002 | Weber et al. ............... 356/236 |

FOREIGN PATENT DOCUMENTS

| WO | WO 97/07627 | 2/1997 |
|---|---|---|
| WO | WO 98/58682 | 12/1998 |

* cited by examiner

*Primary Examiner*—Hoa Q. Pham
(74) *Attorney, Agent, or Firm*—Graybeal Jackson Haley LLP

(57) ABSTRACT

A test and measurement system to assess performance characteristics of an endoscope or other optically based diagnostic or treatment devices. The performance characteristics can include the photometric characteristics, the imaging characteristics and the physical characteristics of the structural elements including mechanical, pneumatic and fluidic systems. The system comprises software and related devices for calibrating the measurement devices, collecting and controlling measurements, analyzing measurements and comparing them to established performance criteria. The system also analyzes previous measurements and provides analysis and reports to assess trends and plan for replacement or servicing.

13 Claims, 6 Drawing Sheets

APPARATUS AND METHODS FOR EVALUATING PERFORMANCE OF ENDOSCOPY DEVICES AND SYSTEMS

CROSS-REFERENCE TO RELATED APPLICATIONS

The present application is a divisional patent application of U.S. patent application Ser. No. 09/661,602, filed Sep. 14, 2000. now U.S. Pat. No. 6,734,958 which claims priority from U.S. provisional patent application No. 60/154,497, filed Sep. 17,1999.

BACKGROUND OF THE INVENTION

Endoscopes are optical instruments that permit a user to see around or through an obstruction, to see something that would otherwise be concealed. For example, endoscopes are used to permit doctors to see inside a patient's body without major surgery; some endoscopes require a small access incision to be made in the patients body. Endoscopy systems typically comprise an illumination light source, illumination light guides to conduct the illuminating light to the tissue under observation, imaging optics, and image collection light guides to conduct the image of the tissue to the observer. The image can be detected by the human eye or by an imaging device such as a CCD camera. An imaging device usually employs an image display system such as a CRT monitor to relay the image to the human eye. In some cases, the image detected by the imaging device or camera may be digitized, stored in memory or on media, processed with various software algorithms, and/or then converted to an analog video signal that can be displayed on the image monitor.

Physicians and surgeons use endoscopy devices to examine tissue and decide on treatment. Having a sound basis to compare normal and abnormal tissues is essential. If changes occur in the way the system presents the visual information, the physician's or surgeon's ability to interpret results is compromised. To assist accurate diagnosis and treatment, hospitals and clinics must have ways to measure and quantify the performance characteristics of endoscopy devices and of the systems comprising such devices.

Components of endoscopes, and endoscopy systems, can become degraded, or can be incorrectly adjusted, or can fail to operate or otherwise fail to perform. It can be difficult to determine if an endoscope is not performing adequately, particularly where the problem comprises inaccurate color representation. Problems arise from a variety of sources, including difficulties with intensity or spectral characteristics of the illumination lamp or light transmission elements, and bad image sensors, software programs or display systems. Other systems can also fail, such as air, water and suction lines.

Endoscopes typically have problems in one of three areas. First is image quality, which can be defined as the accuracy with which the image viewed by the operator represents the target under observation. In other words, does a straight line stay a straight line when viewed through the endoscope? Second is the photometric quality of an image, which can be defined as the spectral distribution of the light emitted from the target. Third, is the physical integrity of the equipment, particularly the endoscope itself, which can sustain optical damage, leaks or blockages in air and fluid lines and damage to the mechanical control components or envelope.

A variety of approaches have been pursued to remedy these problems. See, e.g., U.S. Pat. No. 5,820,547; U.S. Pat. No. 5,841,525; "The Endo Tester™—A Lab VIEW-Based Automated Test System for Fiber-Optic Endoscopes" by Eric Rosow, Hartford Hospital, and Joseph Adam, Premise Development Corporation (brochure); PCT WO 97/07627 (EP0845187 A 19980603); U.S. Pat. No. 5,369,481; U.S. Pat. No. 5,738,824; WO 98/58682); U.S. Pat. No. 5,494,530.

However, there has gone unmet a need for improved apparatus and methods for assessing the color, image or structural characteristics of an endoscope. The present invention provides these and other advantages.

SUMMARY OF THE INVENTION

The present invention provides computer controlled measurement devices, with associated mechanical adapters for connection to various components of endoscopy systems, that measure performance characteristics of an endoscope such as the color, image and structural characteristics. The present invention also provides computer-implemented programming, such as software, for calibrating the measurement devices, collecting and controlling measurements, analyzing measurements or comparing them to established performance criteria. In addition, the systems, devices and methods of the present invention can track previous measurements for a particular endoscope and provide analysis and reports, etc., to identify or describe performance trends and allow a user to plan for replacement or servicing.

In one aspect, the present invention provides a test system able to assess photometric performance characteristics of an endoscope comprising: a photometric measurement module comprising a measurement integrating sphere and at least one adapter able to optically connect the integrating sphere to a plurality of different optical ports of different endoscopes. The photometric measurement module measures data from at least one photometric characteristics selected from the group consisting of absolute optical intensity, relative optical intensity, optical power, optical energy, illuminance, radiance, irradiance, display color, perceived color and transmittance, and a controller containing computer-implemented programming that controls at least one of the calibration, measurement and analysis of the photometric performance characteristics of an endoscope using the data from the module.

In this and other aspects of the invention (unless expressly stated otherwise or clear from the context, all embodiments of the present invention can be mixed and matched), the data are measured over a plurality of discrete wavelengths or wavelength regions, and the system can further comprise an image quality measurement module comprising at least one adapter able to optically connect the module to a plurality of different endoscopes, wherein the module measures data from at least one image quality performance characteristic selected from the group consisting of image size, spatial distortion, contrast, brightness, image resolution, focus and modulation transfer function, and the controller contains computer-implemented programming that controls at least one of the calibration, measurement and analysis of the image quality performance characteristics of an endoscope using the data from the module.

The system can also comprise a structural element measurement module comprising at least one adapter able to operably connect the module to a plurality of different endoscopes, wherein the module measures data of structural element performance characteristic selected from at least one of a mechanical, a pneumatic and a fluidic system of an endoscope, and the controller contains computer-implemented programming that controls at least one of the calibration, measurement and analysis of the structural element performance characteristics using the data from the module.

In some embodiments, the controller controls data acquisition by the photometric measurement module, the image quality measurement module and the structural element measurement module. The controller may track performance trends over time of at least one of the characteristics, respond to a set of operator input instructions to control the data acquisition and analyses of the measurement modules, and calibrate a response of the modules. Calibration can comprise using a reference standard to provide calibration correction factors, and application of the calibration correction factors to the data collected by the photometric measurement module, the image quality measurement module or the structural element measurement module provide a corrected data set. The computer-implemented programming may also provide for acquisition and storage of a background signal data set; acquisition and storage of a measurement signal data set representing raw data obtained from the sample device; and, subtraction of the background signal data set from the measurement signal data set to generate a background corrected measurement data set.

If desired, the programming can apply the calibration correction factors to the background corrected measurement data set to generate a calibrated measurement data set. It may also analyze the background corrected measurement data set to determine if the background corrected measurement data set is of acceptable quality to provide an acceptable background measurement data set and provides an indicator to the operator if the background corrected measurement data set is not of acceptable quality, and analyze the background corrected measurement data set with the calibration measurement data set and provides an indication of a performance characteristic for at least one of the characteristics based on the background corrected measurement data set with the calibration measurement data set. The programming may determines whether the performance characteristic is within an acceptable range. The performance characteristic, and other data and programming, can be recorded in a computer-readable memory, for example recording the performance characteristic can provide a recorded measurement data set.

The programming additionally compares and analyzes a performance characteristic from a recorded measurement data set and at least one additional performance characteristic from a different time to determine a temporal trend, which can, as with the other data, analyses, results and other information related to the system, be indicated to the user. The programming may analyze the data obtained from the modules to determine if the data comprises an acceptable signal level and if not then adjust data acquisition until the acceptable signal level is obtained.

In preferred embodiments, the structural element measurement module comprises a pressure transducer and a flow meter, and the adapter operably connects the structural element measurement module to an endoscope to transfer a gas, a liquid or a vacuum between the structural element measurement module and the endoscope. The photometric measurement module preferably comprises a spectrometer comprising a wavelength dispersive element optically connected to the measurement integrating sphere. The at least one adapter may comprise a set of removable adapters able to optically connect to a plurality of light-emitting ports of a plurality of different endoscopes; the removable adapters comprise a flexible fiber optic or a liquid light guide. The system preferably comprises an illumination light source having a known spectral distribution and an illumination integrating sphere optically connected to the illumination light source, for example by a flexible fiber optic, a liquid light guide, a condenser lens assembly, a mirror or a prism.

In certain embodiments, the mating surface of the removable adapters that mates with an interior surface of the integrating sphere comprises a curvature that substantially matches the curvature of the interior surface, such that the mating surface lies substantially flush with the interior surface. The removable adapter can comprise a first mating surface sized to a the first integrating sphere and a second mating surface sized to fit a second integrating sphere.

The image quality measurement module comprises a linearly arrayed sensing element such as a line scan CCD detector and a linear diode array. The linearly arrayed sensing element may be translated or rotated relative to a conjugate image plane of the endoscope to make at least one measurement in the conjugate image plane, or vice-versa, and the programming can reconstruct a sequence measurements of in the conjugate image plane to create a two-dimensional digital image of the conjugate image plane.

In another aspect, the present invention provides a photometric measurement system comprising an integrating sphere optically connected to a receive light from a measurement probe sized that is shaped to receive light from an image display screen, the integrating sphere further optically connected to transmit light to a photometric measurement device comprising a spectrometer comprising a wavelength dispersive element, wherein the photometric measurement system is operably connected to a controller containing computer-implemented programming that responds to a set of operator input instructions to control the data acquisition and analyses of the photometric measurement system and that controls measurement of the image display screen. In certain embodiments, the image display screen is operably connectable to an endoscope to display an image transmitted from the endoscope. The image display screen can be operably connectable to a signal generator able to generate a plurality of test signals on the image display screen.

In a further aspect, the present invention provides a photometric system to assess optical characteristics of a light source, the system comprising a photometric measurement module comprising a measurement integrating sphere and at least one light collector sized and shaped to transmit substantially all wavelengths of UV, visible and NIR light from the sample light source to the integrating sphere, the measurement integrating sphere optically connected to transmit substantially all wavelengths of UV, visible and NIR light from the measurement integrating sphere to a photometric measurement device that is able to measure substantially all wavelengths of UV, visible and NIR light. The photometric measurement module is operably connected to a controller containing computer-implemented programming that responds to a set of operator input instructions to control the data acquisition and analyses of the photometric measurement module and that controls measurement and analysis of the sample light source. In certain embodiments, the light collector is sized and shaped to transmit light from an endoscopic light source, and the system can further comprise an adapter to transmit light from the sample light source through the endoscope upstream of the measurement integration sphere.

In still a further aspect, the present invention provides a test and measurement system able to assess performance characteristics of an endoscope comprising a all three of a photometric measurement module (with or without an integration sphere), an image quality measurement module, a structural element measurement module, and related programming.

In still yet another aspect, the present invention provides a removable adapter having a first end and a second end, the first end defining a mating surface that mates with an interior surface of an integrating sphere and comprising a substantially spherical curvature that substantially matches a curvature of the interior surface, such that the mating surface lies substantially flush with the interior surface when the removable adapter is mated with the integrating sphere, and the second end defining a port sized and shaped to optically connect the integrating sphere to a sample device. The present invention also provides an integrating sphere system comprising such a removable adapter In another aspect, the present invention provides a test system comprising an image quality measurement module and a detector comprising a linearly arrayed sensing element. The linearly arrayed sensing element can be a one-line sensor, a three-line sensor or other suitable design. Also, the integrating sphere can comprising at least two optical input ports sized and shaped to optically connect the integrating sphere to at least an equal plurality of different optical ports of an endoscope.

These and other aspects, features and embodiments of the present invention are set forth within this application, including the following Detailed Description and attached drawings. In addition, various references are set forth herein, including in the Cross-Reference To Related Applications, that describe in more detail certain apparatus, methods and other information; all such references are incorporated herein by reference in their entirety and for all their teachings and disclosures, regardless of where they may appear in this application.

BRIEF DESCRIPTION OF THE DRAWINGS

FIG. 3 depicts an overhead plan view

DETAILED DESCRIPTION OF THE INVENTION

Figure 1:
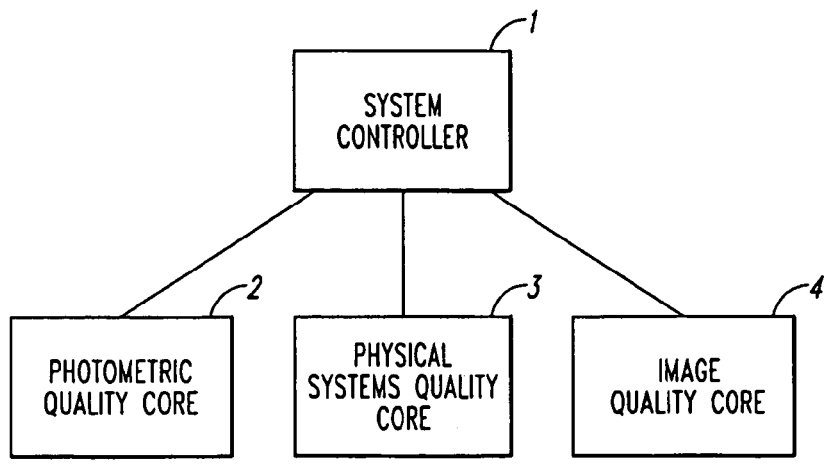
FIG. 1 is a block diagram depicting the major hardware components of a test and measurement system, comprising a system controller, a photometric quality module, a physical systems quality module and an image quality module.

The present invention provides test systems and related methods that are able to provide high-quality measurements and analyses of optical devices, particularly endoscopes so that the performance characteristics can be assessed and tracked. Briefly, in one aspect the present invention provides a system that is able to measure each of the light (e.g., spectral) characteristics, imaging characteristics and structural characteristics of an endoscope. In some embodiments, the module that measures the light characteristics comprises an integrating sphere. Preferably, the system further comprises at least one adapter that optically connects various components and various devices to the integrating sphere. Preferably, there are a plurality of removable adapters so that the integrating sphere or other testing device need have only one or a minimum of input ports, or the adapter can have a plurality of different plug-in modes so that it can accept a plurality of different endoscopes, or the test device can have a plurality of different input or output ports to accommodate different endoscopes.

The present invention also provides computer-implemented programming, such as software, for calibrating the measurement devices, collecting and controlling measurements, analyzing measurements or comparing them to established performance criteria. In addition, the systems, devices and methods of the present invention can track previous measurements for a particular endoscope and provide analysis and reports, etc., to identify or describe performance trends and allow a user to plan for replacement or servicing. In one embodiment, the invention comprises several modular components to allow evaluation of the endoscope. The assessment of the functional characteristics of endoscopes can comprise comparing measurements from the device using measurement standards representing a certain level of performance.

Definitions.

The following paragraphs provide definitions of some of the terms used herein. All terms used herein, including those specifically described below in this section, are used in accordance with their ordinary meanings unless the context or definition indicates otherwise. Also unless indicated otherwise, except within the claims, the use of "or" includes "and" and vice-versa. Non-limiting terms are not to be construed as limiting unless expressly stated (for example, "including" means "including without limitation" unless expressly stated otherwise). "Endoscope" is used herein in its traditional sense to indicate an optical or electronic instrument, typically tubular and elongated, that generally permits a user to see around an obstruction or through an opening in an obstruction, to see something that would otherwise be concealed. Endoscopy systems comprise a collection of equipment used with an endoscope and can provide illumination, insufflation, irrigation, suction, image transmission, image capture, image display, and other functions associated with performing an endoscopic procedure. An endoscopy device is any device or device accessory that is part of an endoscopy system and operably connected to the endoscope. An endoscopic light source is a light source that provides illumination to an endoscope. An endoscopic procedure is any procedure, such as a medical procedure, requiring use of an endoscope. As used herein, unless the context or definition expressly indicates otherwise, reference to an endoscope includes reference to the entire endoscopy system and related endoscopy devices operably connected to the endoscope. "Upstream" and "downstream" are used in their traditional sense wherein upstream indicates closer to a light source, while downstream indicates farther away from a light source. Similarly, "proximal" indicates upstream and "distal" indicates downstream.

A "controller" is a device that is capable of controlling an assay or measurement system of the present invention, including portions thereof such as a photometric measurement module or an image measurement module, or other elements of the apparatus and methods of the present invention. For example, the controller can which data are gathered by a measurement module, can track such data over time for an institution or a particular endoscope, and can analyze or interpret the data. Typically, a controller comprises one or more computers or other devices comprising a central processing unit (CPU) and contains computer-implemented programming that directs the controller, or from which the controller directs other devices, to perform certain functions or actions, such as those functions and actions described herein. A computer comprises an electronic device that can store coded data and can be set or programmed to perform mathematical or logical operations at high speed. Controllers, and appropriate computer-implemented programming associated with such controllers, are either well known in the art or well within the skill of a skilled artisan in view of the present disclosure, and thus selection or creation of a desirable controller or computer-implemented programming for a particular aspect of the present invention is within the scope of the art in view of the present disclosure.

"Photometric measurement module" is used herein to indicate a system, typically comprising an integration sphere and one or more adapters, preferably removable, able to measure the performance characteristics of the photometric features of an endoscope under test, which may also be called a sample endoscope, such as color and intensity.

"Image quality measurement module" is used herein to indicate a system, able to measure the performance characteristics of the image quality of a endoscope under test, such as accurate representation of lines in the image.

"Structural element measurement module" is used herein to indicate a system, able to measure the performance characteristics of a endoscope under test, such as the performance of the gas, fluidic and vacuum systems of the endoscope.

Unless otherwise defined in the text, terms relating to measurement and characterization of light are used in their traditional context, for example as set forth in the Handbook of Optics, CD-ROM Second Edition, sponsored by the Optical Society of America and published by McGraw-Hill, 1996.

The terms set forth in this application are not to be interpreted in the claims as indicating a "means plus function" relationship unless the word "means" is specifically recited in a claim, and are to be interpreted in the claims as indicating a "means plus function" relationship where the word "means" is specifically recited in a claim. Similarly, the terms set forth in this application are not to be interpreted in method or process claims as indicating a "step plus function" relationship unless the word "step" is specifically recited in the claims, and are to be interpreted in the claims as indicating a "step plus function" relationship where the word "step" is specifically recited in a claim.

Other terms and phrases in this application are defined in accordance with the above definitions, and in other portions of this application.

Figure 2:
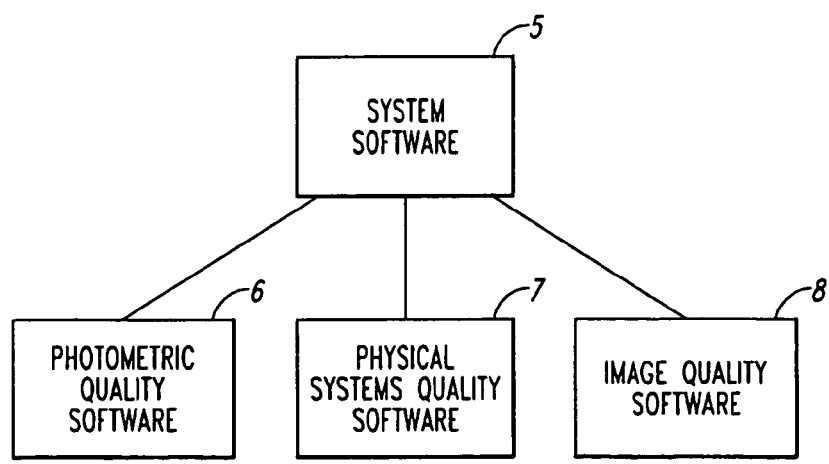
FIG. 2 is a block diagram showing software components of the system, including the core system software, photometric quality software, physical systems quality software, and image quality software.

The figures depict representative examples of the present invention. FIG. 1 is a block diagram of one embodiment of a test and measurement system. The system comprises one or more core modules operably connected to a controller containing desired computer-implemented programming. In FIG. 1, photometric measurement module 2, image quality measurement module 3 and structural element measurement module 4 are operably connected to a system controller 1. Hardware and software, or computer-implemented programming, components can be added to the core modules to enable a variety of measurements and to interface the measurement modules to various endoscopy devices and systems. The computer can be any desired computer, such as a laptop or portable computer equipped with commercially available operating system software such as Windows 98 (Microsoft, Redmond Wash.). FIG. 2 shows the software architecture of one embodiment of the system that comprises core system software 5, a photometric module software 6, a physical systems module software 7, and an image quality module software 8. System controller 1 may comprise a commercially available computer and associated commercially available peripheral equipment and operating system software, measurement system software 5 and measurement module control and analysis software 6, 7, 8.

Figure 3:
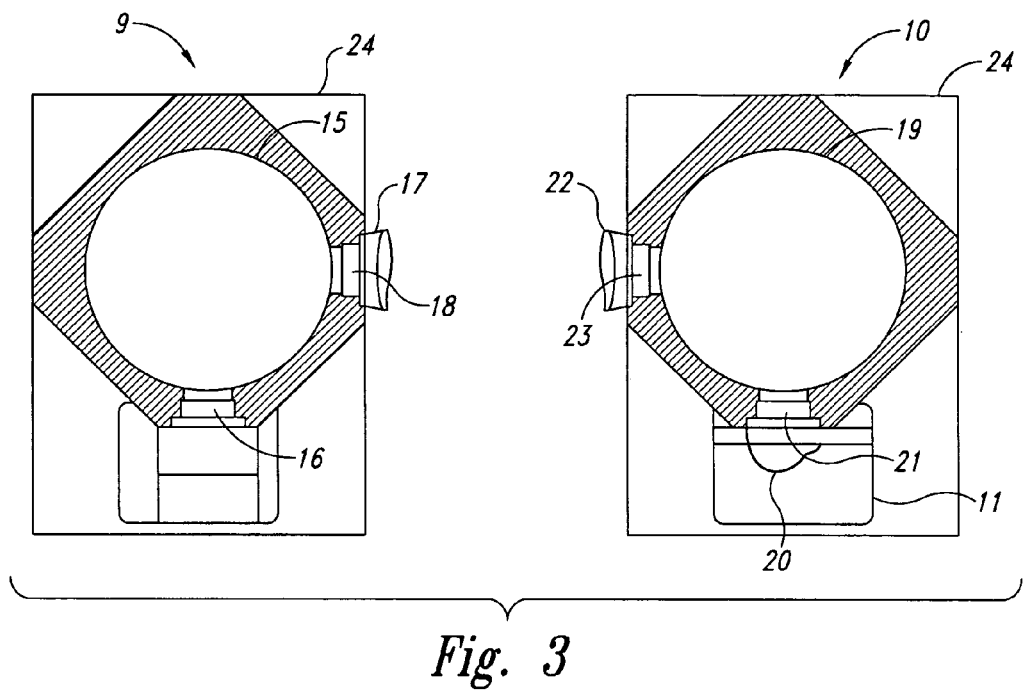
FIG. 3 are schematic diagrams depicting in partial cross-section various hardware components of the photometric quality module.
Figure 4:
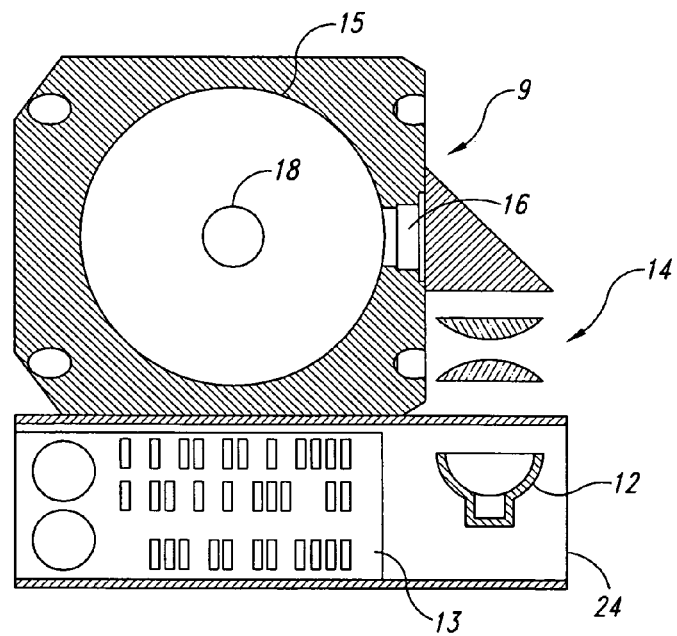
FIG. 4 depicts a second side view of an illumination unit wherein the unit has been rotated 90° relative to FIG. 3.

FIGS. 3, and 4 show different features of a photometric measurement core module. The module in the figures comprises an illumination unit 9 and photometric measurement unit 10, each disposed upon a base 24. FIG. 3 depicts an overhead view, and FIG. 4 depicts a side view of an illumination unit from FIG. 3. Referring generally to both Figures, photometric measurements are made using a spectrometer 11, preferably calibrated and under software control. The light source 12 and the spectrometer 11 are optically connected to illumination integrating sphere 15 and measurement integrating sphere 19 to minimize structural or directional aspects of the emitted light (for the illumination integrating sphere 15) or collected light (measurement integrating sphere 19) by spatially averaging the emitted and collected light. Such structural or dimensional effects can increase measurement artifacts and reduce the repeatability and reliability of a measurement. An illumination integrating sphere provides light to a sample device, while a measurement integrating sphere receives light from a sample device.

The photometric, or light, measurement unit 10 can be used alone or with illumination unit 9 to measure photometric quality of optical devices such as endoscopy light sources, photo-therapy lamps, and image display monitors. Briefly, photometric measurement unit 10 measures the transmission characteristics of the illumination and imaging guides and systems of such devices. The integrating spheres are preferably equipped with a standardized port sized to accept a series of removable adapters that are in turn sized to couple with a plurality of devices.

In FIG. 3, illumination unit 9 comprises an illumination integrating sphere 15 and photometric measurement unit 10 comprises a measurement integrating sphere 19. The interior surface of illumination integrating sphere 15 and measurement integrating sphere 19 is fabricated from or coated with a material with desirable reflection characteristics. Suitable material is known in the art (Labsphere, Inc., North Sutton, N.H.). The illumination energy, or light, is spatially averaged by multiple internal reflections within the integrating sphere until it exits an optical port via removable illumination adapter 17 mounted in illumination adapter port 18. Optical port indicates a port, typically an opening, in for the transmission of light into or out of a device. Typical optical ports include the tip and ocular of an endoscope, and the illumination coupler of an endoscope or integrating sphere. Removable adapter 17 represents one of a set of adapters designed to mate with adapter port 18 and the endoscopy device under test and to transmit light from the illumination integrating sphere 15 into the endoscopy device, or from the endoscopy device to measurement integrating sphere 19 if desired. Corresponding removable measurement adapter 22 is mounted in measurement adapter port 23 of measurement unit 10. Light for testing an endoscope is provided from a light source 12, shown in FIG. 4, which then enters illumination integrating sphere 15, is spatially averaged, then transmitted via removable adapter 17 mounted in adapter port 18 to the sample endoscope. Removable adapter 17 is one of a set of adapters designed to mate with adapter port 18 and the endoscope and to transmit light from the illumination integrating sphere 15 to the endoscope.

In photometric measurement unit 10, measurement integrating sphere 19 sits atop a spectrometer 11, preferably calibrated, which is optically connected to spectrometer port 21 of measurement integrating sphere 19 by light guide 20. Light from the sample endoscope under test enters measurement integrating sphere 19 through removable adapter 17 which is mounted in measurement adapter port 18. Removable adapter 17 is one of a set of adapters designed to mate with adapter port 18 and the endoscopy device under test and to transmit light from the endoscopy device under test into the integrating sphere 19. This light from the endoscope is spatially averaged by multiple internal reflections in the integrating sphere until it exits via the flexible light guide 20 and is conducted to the spectrometer 11. Light guide 20 can be any type of light guide, preferably flexible, such as a liquid light guide, optical fiber, optical fiber bundle or a hollow fiber, hollow reflective light guide, or a lens system, or an other system that conducts light from one location to another, preferably without introducing and artifacts into the light. An optical fiber is a fiber composed of two concentric regions of optically transmissive material with different refractive indices that transmits light axially by internal reflection at the boundary of the two materials. In the case of gradient refractive index material this boundary may be diffuse rather than abrupt.

Spectrometer 11 comprises an entrance port and optics to direct the beam to a wavelength dispersive grating and then to a CCD array detector, where the optical energy is transduced into electrical energy which can be measured. The array detector signal can be calibrated for wavelength and photometric response over a suitable wavelength range in the UV, Visible or NIR regions of the electromagnetic spectrum. Such spectrometers are known in the art and are commercially available from manufacturers such as Ocean Optics of Dunedin, Fla. Other wavelength dispersive elements including prisms are known in the art and can also used. Other transducing detectors and detector arrays are known in the art and can also used. Spectrometer 11 is electrically connected to a serial interface board which performs analog to digital conversion of the measurement signal and then transfers this digital information via a data cable to the serial data port of the system controller 1, depicted in FIG. 1. Other architectures of analog to digital signal conversion and of digital data transfer to the system controller are known in the art and can also used.

In FIG. 4, the illumination unit 9 comprises a lamp as a light source 12, a power supply 13 for the lamp, an optical relay system 14, and an illumination integrating sphere 15 equipped with two optical access ports 16, 18. Light source port 16 accepts illumination energy from light source 12 via optical relay system 14.

A variety of removable illumination and measurement adapters 17 are preferred to connect to various endoscopes to be tested. Typical adapters include adapters sized to fit endoscope/light-source connectors, endoscope oculars, endoscope distal tips (i.e., the end of the endoscope inserted into the body), endoscope oculars, endoscopy light sources, image display monitors, lamps and calibration light guides.

Figure 5:
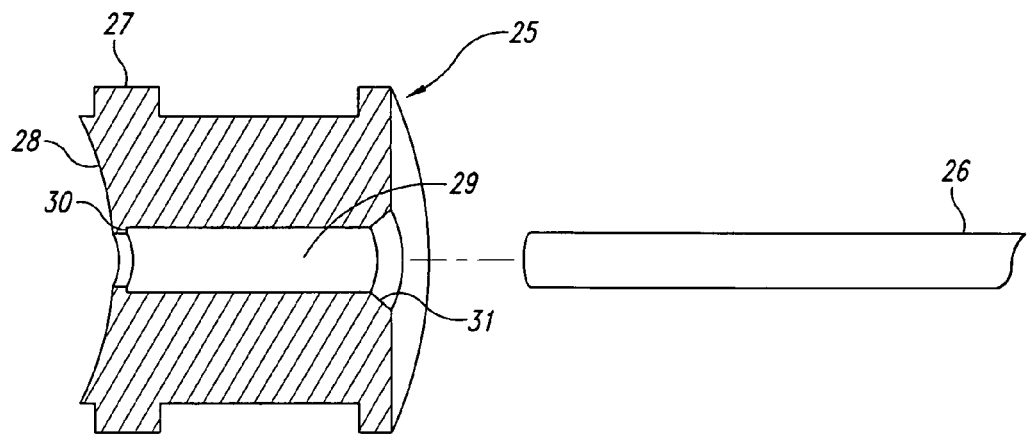
FIG. 5 is a schematic diagram depicting a partial cross-sectional view of an adapter that allows coupling of distal viewing tip or objective end of an endoscope to an integrating sphere.

FIG. 5 shows a partial cross-sectional view of an endoscope distal tip adapter 25 that mates an endoscope tip 26 with a removable adapter 17, 22 or an adapter port 18, 23 of the respective integrating spheres. The adapters of the present invention, such as endoscope distal tip adapter 25 are substantially cylindrical as depicted, but other shapes can also be used. Adapters such as endoscope distal tip adapter 25 can be formed as a single component or in two or more components. Indexing projection 27 mates with a corresponding channel in the integrating sphere port to guide the adapter when it is inserted. In this embodiment the guide path is helical but this need not be so in all embodiments. When inserted to the end of the guide path, indexing projection 27 comes to rest against a stop in the adapter port 16 of the integrating sphere that preferably causes spherically curved surface 28 of the adapter to be flush with the interior surface of the integrating sphere. Other mechanical mating structures can also be used. Curved surface 28, as with other adapters depicted herein, is preferably coated with, or fabricated from, the same reflective material as the interior surface of the integrating sphere. Endoscope distal tip adapter 25 has a concentric cylindrical channel 29 that allows the an endoscope tip 26 to be inserted until it contacts mechanical stop 30. The channel dimensions and dimensions of stop 30 vary depending on the make and model of the endoscope to be tested. Channel 29 has a tapered input portion 31 to guide the endoscope into the channel and to prevent damage to the tip of the endoscope, as it is inserted.

Figure 6:
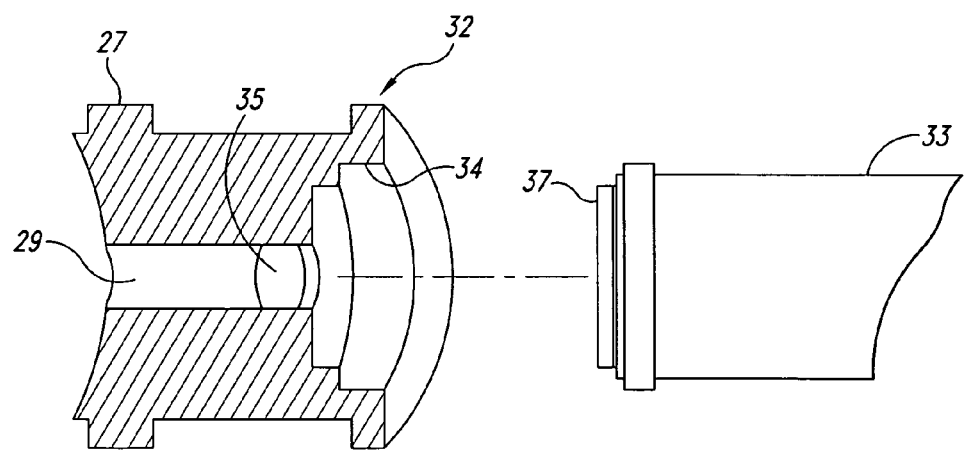
FIG. 6 is a schematic diagram depicting a partial cross-sectional view of an adapter that allows coupling of an endoscope ocular to an integrating sphere.

FIG. 6 shows an ocular adapter 32 that mates an endoscope ocular or image port with a removable adapter 17, 22 or adapter port 18, 23 of the integrating spheres 15, 19 shown in FIGS. 3–4. The surfaces of ocular adapter 32 that mate with integrating sphere adapter port 18 has similar structures as shown for endoscope tip adapter 25. Ocular adapter 32 has a concentric cylindrical channel 29 that allows light from the ocular of the endoscope under test to be directed into or out of the integrating sphere by relay lens or lens assembly 35. The surfaces of ocular adapter 32 that mate with ocular 33 and ocular end 37 of the endoscope are sized to fit the ocular under consideration. Ocular end 37 is removably, optically connected to connector portion 34. Channel 29 can comprise one or more relay lenses, mirrors or other optical elements suitable for a specific endoscope if desired.

Figure 7:
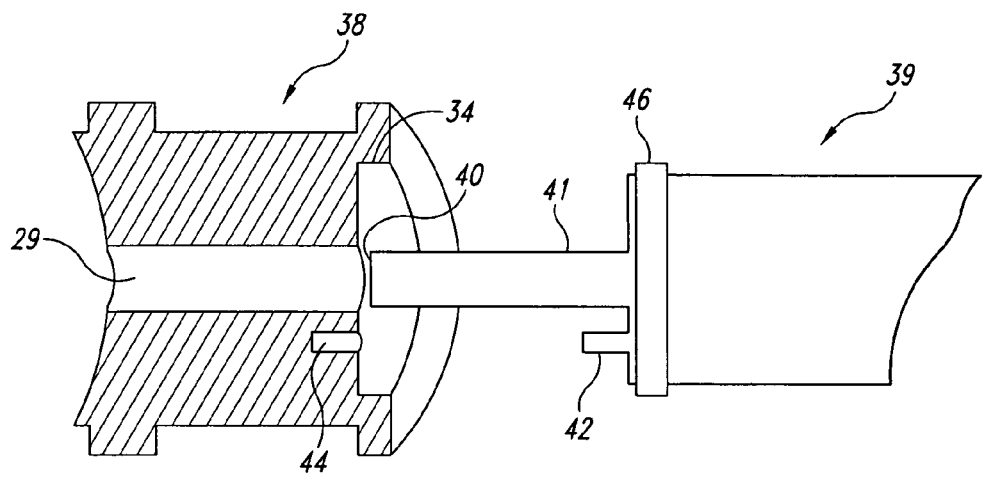
FIG. 7 is a schematic diagram depicting a partial cross-sectional view of an adapter that allows coupling of a light source connector on an endoscopic to an integrating sphere.

FIG. 7 shows an endoscope light source adapter 38 that mates an endoscope light source connector 39 with an adapter port of the integrating spheres 15, 19 shown in FIGS. 3–4. Light source adapter 25 has a concentric cylindrical channel 29 that allows the light source connector barrel 41 of the sample endoscope be inserted to an appropriate position to allow light to be directed through light source optical port 40 into or out of the integrating sphere either directly or by a relay lens or lens assembly. The channel dimensions vary depending on the make and model of light source connector barrel 41. Some endoscope light source connectors incorporate one or more structural systems connectors 42 for fluid, vacuum or air delivery. Accordingly, endoscope light source adapter 38 may incorporate one or more receptacles or guides 44 to allow insertion of the device to be tested. The light source connector 46 of the endoscope or other device to be tested is removably connected to connector portion 34 of light source adapter 38. As with other connectors and adapters according to the present invention, connector portion 34 is sized and shaped to mate with light source connectors of a plurality of endoscopes. Channel 29 can comprise one or more relay lenses, mirrors or other optical elements suitable for a specific endoscope if desired. Light source connector 39 comprises a light collector that collects light from the sample device and transmits substantially all wavelengths of UV, visible and NIR to a measurement module, typically via an optical fiber or other flexible light guide sized and shaped to transmit. Such light collectors can be used with other embodiments of the present invention.

Figure 8:
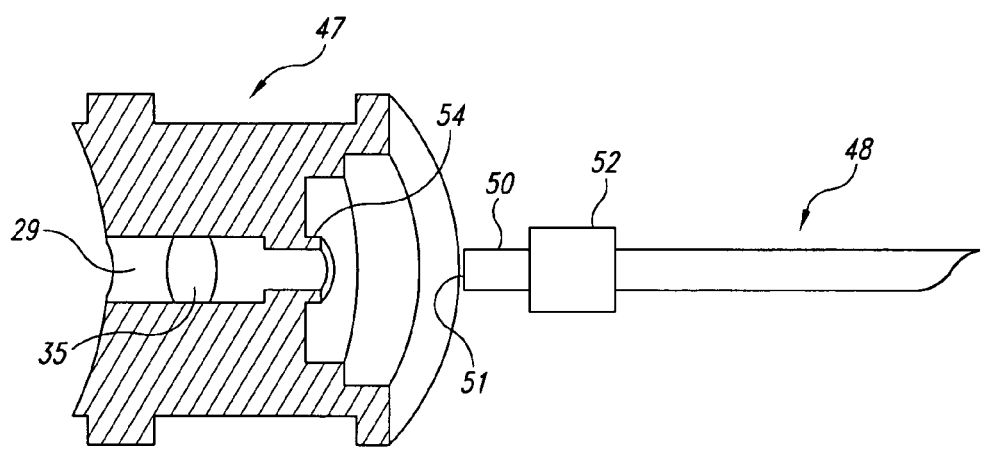
FIG. 8 is a schematic diagram depicting a partial cross-sectional view of an adapter that allows coupling of a calibration light guide to an integrating sphere.

FIG. 8 shows a light guide connector adapter 47 that mates light guide 48 to an adapter port. Light guide 48 may be a flexible or rigid fiber optic or liquid light guide. Light guide connector adapter 47 may also be connected to a spectrometer port, light source port or other optical element having a shape similar to a light guide. Light guide connector adapter 47 has a concentric cylindrical channel 29 that allows the light guide barrel 50 to be inserted to an appropriate position to allow light to be directed through fiber optical port 51 into or out of the integrating sphere either directly or by a relay lens or lens assembly 35. The channel dimensions vary depending on the make and model of light guide 48. Connector 52 of light guide 48 is removably connected to connector portion 54. Channel 55 can comprise one or more relay lenses, mirrors or other optical elements suitable for a specific endoscope if desired.

Figure 9:
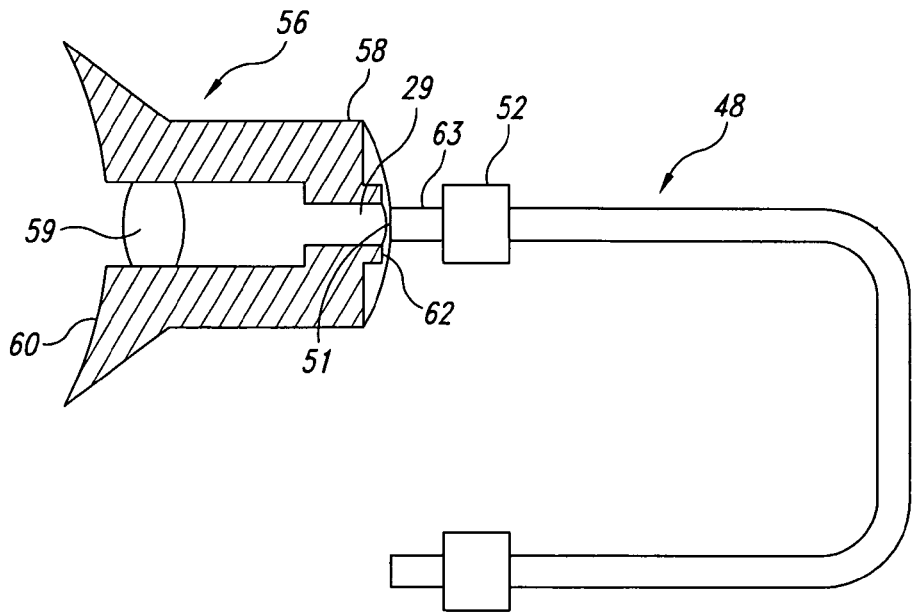
FIG. 9 is a schematic diagram depicting a partial cross-sectional view of an adapter that allows coupling of an image display monitor to an integrating sphere.

FIG. 9 shows a partial cross-sectional view of display monitor measurement adapter 56 that connects to light guide 48 that may in turn be connected to light guide connector adapter 47 as in FIG. 7. Display monitor measurement adapter 56 is an example of a probe, which is a device optically connected to a measurement device, and if desired also to an illumination device, and able to obtain data from an externally located sample device. The probe comprises a light collector that collects light from the sample device and, typically, is connected via an optical fiber or other flexible light guide. Display monitor measurement adapter 56 comprises a cylindrical component 58 plus collection lens 59 and elastomeric suction cup 60. Display monitor measurement adapter 56 has a concentric cylindrical channel 29 that allows the light guide connector barrel 63 of light guide 48 to be inserted to an appropriate position to allow light emanating from the display monitor to be directed through fiber optical port 51 into the light guide either directly or by a relay lens or lens assembly. The channel dimensions vary depending on the make and model of light guide 48. The connector 52 of the light guide is removably connected to connector projection 62. Channel 29 can comprise one or more relay lenses, mirrors or other optical elements suitable for a specific endoscope if desired.

Figure 10:
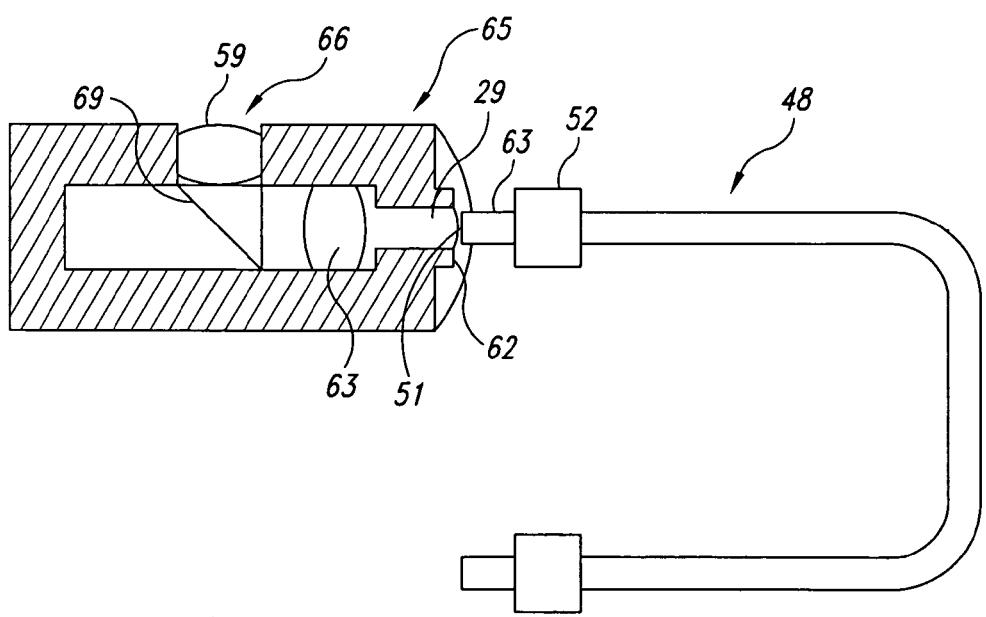
FIG. 10 is a schematic diagram depicting a partial cross-sectional view of an adapter that allows measurement of illumination at a surface by an integrating sphere.

FIG. 10 shows a partial cross-sectional view of an area illumination measurement adapter 65 that connects to light guide 48 that may in turn be connected to light guide connector adapter 47 of FIG. 7. Area illumination measurement adapter 65 collects light through aperture 66 and collection lens 67. The light is then re-directed 90° by beam-steering prism 69, through focusing lens 68 through cylindrical channel 29 into fiber optical port 51 and light guide connector barrel 63, which barrel can be inserted into cylindrical channel 29. Beam-steering prism 69 may be replaced by a mirror or other beam-steering device. The connector 52 of the light guide is removably connected to connector projection 62. Cylindrical channel 29 can comprise one or more relay lenses, mirrors or other optical elements suitable for a specific endoscope if desired.

Figure 11:
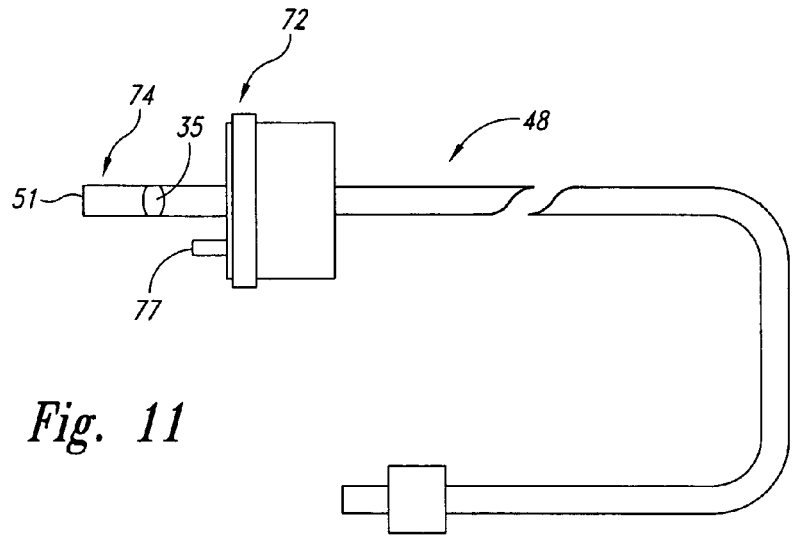
FIG. 11 is a schematic diagram depicting a partial cross-sectional view of an adapter that allows coupling of an endoscope light source to an integrating sphere.

FIG. 11 shows a partial cross-sectional view of an endoscope illumination system measurement adapter 72 that connects to light guide 48, which may in turn be connected to light guide connector adapter 47 of FIG. 7. Endoscope illumination system measurement adapter 72 has an approximately concentric cylindrical light source adapter connector barrel 74 that can be inserted into an endoscope illumination source connector where the endoscope light guide connector would normally be inserted. The adapter barrel is inserted to an appropriate position to allow light to be directed through fiber optical port 51 and either directly or by a relay lens or lens assembly 35 into light guide 48. Some endoscope light source connectors incorporate one or more additional connectors for fluid, vacuum or air delivery. An endoscope illumination system measurement adapter 72 for such endoscopes may incorporate one or more barrels or ports 77 to allow insertion into or connection to endoscope.

Turning now to additional discussion of the computer-implemented programming provided by the present invention, the programming for the photometric measurement module controls one or more of the spectrometer data acquisition parameters, the transfer of data from the spectrometer, and the processing and analysis of the spectrometer data. Typically, the programming comprises algorithms, which are a set of rules and/or a sequence of procedures implemented in software. Control of the spectrometer or other system device means software algorithms that cause the computer to transmit and receive electronic signals that initiate actions at or report status of the device. The spectrometer measurement data comprises an array of numbers representing the intensity of light impinging on a detector element positioned to receive light from a particular wavelength range. The programming of this and other embodiments can respond to automated instructions or to operator input instructions.

Light entering the spectrometer encounters a wavelength dispersive optical element that distributes the light by wavelength across a detector array. The detector array converts the optical energy of the photons striking the detector into electrical energy. The detector elements can be calibrated for the wavelength of light by injecting light from a source of known discrete wavelengths such as a mercury-argon lamp into the detector. A discrete wavelength of light generally means light of a particular energy level, for example emitted from a specific electron transition of a particular element or molecule. Such discrete wavelength sources are know in the art and are commercially available from manufacturers such as Ocean Optics of Dunedin, Fla. The programming for the photometric measurement module can use mathematical regression techniques to calculate wavelength range values for each detector element.

After the wavelength response of the spectrometer is calculated, the programming may calibrate the photometric intensity response of the detector at each nominal measurement wavelength. The nominal measurement wavelength is the mean wavelength of the wavelengths impinging on a given detector element. The algorithm for photometric calibration can acquire data for a dark spectrum over a specific interval of time. The dark spectrum is a data array that represents the signal response of the spectrometer detector elements when no light is introduced. Light is then introduced to the photometric measurement module from a calibrated source. The calibrated source (Gamma Scientific, California) emits a smoothly varying spectrum of light of know intensity at a range of wavelengths. The photometric measurement module software acquires spectral data from this source for the same specific interval of time as the dark spectrum and then the photometric calibration software subtracts the dark spectrum from the intensity calibration spectrum and then calculates an intensity calibration factor for each wavelength element.

The programming can also calibrate the measurement system using reference standards to generate calibration correction factors, which represent the difference between the expected signal for the reference standard and the actual signal. The programming may then adjust measurements or data from the sample device, typically by multiplying the data from the sample by the calibration correction factors, to provide a corrected data set. The computer-implemented programming can additionally apply the calibration correction factors to the background corrected measurement data set to generate a calibrated measurement data set, and can also analyze the background corrected measurement data set to determine if the background corrected measurement data set is of acceptable quality to provide an acceptable background measurement data set. An indicator, such as a note on a computer screen, a blinking light or a sound, can be provided to the operator if the background corrected measurement data set, or other desired data set, is not of acceptable quality.

The background corrected measurement data set can be analyzed with the calibration measurement data set to provide an indication of a performance characteristic for the photometric characteristics, the image quality characteristics and the structural element characteristics, preferably all of the characteristics under investigation. If desired, the computer-implemented programming can determine whether the performance characteristic is within an acceptable range, and the data and the results can be recorded, for example in a computer-readable memory, to provide a recorded measurement data set. The recorded measurement data set can be examined to determine a temporal trend for the characteristics under investigation. If the data is not at an acceptable signal level, the controller or user can adjust data acquisition parameters until the acceptable signal level is obtained.

In some embodiments, the structural element measurement module comprises a pressure transducer and a flow meter, and the adapter operably connects the structural element measurement module to an endoscope to transfer a gas, a liquid or a vacuum between the structural element measurement module and the endoscope. The photometric measurement module typically comprises a spectrometer comprising a wavelength dispersive element, such as a prism, optically connected to the measurement integrating sphere. The system typically comprises a reference illumination light source having a known spectral distribution and an illumination integrating sphere optically connected to the illumination light source. The illumination integrating sphere can be optically coupled to the illumination light source by a flexible fiber optic, a liquid light guide, a condenser lens assembly, a mirror or a prism.

In some embodiments, the mating surface of the removable adapters that mates with the interior surface of the illumination integrating sphere or the measurement integrating sphere comprises a curvature that substantially matches the curvature of the interior surface, such that the mating surface lies substantially flush with the interior surface. The removable adapter can comprise a first mating surface sized to fit a first integrating sphere and a second mating surface sized to fit the second integrating sphere.

The photometric calibration software may also adjust the intensity calibration factor for a range of measurement integration times, to effectively extend the dynamic range of the measurement module. The photometric measurement module can be used for measurements once it is wavelength and intensity calibrated. Measurement of light with an intensity and wavelength calibrated spectrometer may be referred to as spectro-radiometry. Relating spectro-radiometric measurements to the observer characteristics of the human eye is referred to as photometry. Photometric measurements may be classified as absolute optical intensity, relative optical intensity, optical power, optical energy, illuminance, radiance, irradiance, display color (the color on a display screen), perceived color (the color seen by a human user through a solely optical system, wherein the light has not been converted into any other medium, such as an electrical signal) and transmittance and may be made over a plurality of discrete wavelengths or wavelength regions. Absolute optical intensity is measurement of the number of photons striking a given area for a given period of time. It can be expressed in a variety of combinations of units. Relative optical intensity is the relative intensity of one measurement to another measurement. An example of this is the comparison or ratio of the measured intensity at one wavelength relative to the measured intensity at another wavelength. A wavelength region means light comprised of photons with wavelengths bounded by a shorter and a longer limiting wavelength or upper and lower limiting energy level.

Measurement of light source emissions from endoscopy illumination devices, therapeutic lamps or illumination systems or image display monitors are accomplished by utilizing the measurement unit of the photometric measurement module and the appropriate adapter and software. The light guide adapter is connected to the input port of the measurement integrating sphere and the endoscope illumination system measurement adapter is connected to distal end of the light guide and then inserted into the endoscope light guide port of the light source to be measured.

As with other embodiments of the invention, the user or other initiator preferably begins a measurement after the measurement system and the device to be measured has had time to reach environmental equilibrium. The measurement software then acquires measurement data. An auto-ranging algorithm evaluates the data to determine if the measurement is of sufficient signal strength and then adjusts measurement integration time until the signal is suitable or an error code is generated. The light source is then turned off or shuttered and a dark spectrum or background measurement is taken, preferably with the same integration time as for the light source measurement, to provide a background signal data set. The measurement algorithm then subtracts the dark spectrum or background measurement from the light source measurement. The system also acquires, and preferably stores, a measurement signal data set representing raw data obtained from the sample device. The background signal data set is subtracted from the measurement signal data set to generate a background corrected measurement data set. The system can also apply wavelength and intensity calibration factors. The various data can be read-out or stored in computer-readable memory, such as an electronic database for analysis.

The analysis software compares characteristics of the measurement spectra to predetermined characteristics that define an acceptable quality measurement. Such features may include signal magnitude, signal-to-noise ratio and relative distribution of wavelengths. Analysis comprises comparing a measurement feature to acceptable upper or lower threshold values for that measurement, or applying a linear discriminant function, or a neural network discriminant function to a set of measurement features. If the measurement is not considered acceptable the measurement is flagged in the electronic database and the user is notified of the failure and requested to take appropriate action such as taking another measurement.

If the measurement is considered acceptable, the analysis software compares the values of characteristic features of the measurement spectra to threshold values of features that identify acceptable performance levels for the light source or device being measured. These values are presented to the user via the system controller display and are recorded electronically in the device database. Any failures to meet acceptable performance levels for the device being measured are preferably identified and reported to the user.

The analysis software then compares the measurement to previous measurements of the device to determine the temporal trend for at least one performance characteristic of the endoscope. The programming can produce a report that graphically represents the trend of the device characteristics.

Measurement of an endoscopy image display monitor or screen can be accomplished similarly. Image display screens include cathode ray tubes, flat panel displays, such as liquid crystal or TFT displays, and projected displays. A cathode ray tube is a vacuum tube that accelerates a stream of electrons from an electron gun to a phosphor screen and uses field coils to direct the beam so it scans and creates an image. A flat panel display is a semiconductor based image display device such as a TFT display or a LCD display that is typically flat and does not employ a CRT to create the image. The steps of acquiring a dark spectrum and a measurement spectrum do not require the shuttering of the display, but preferably involve using a signal generator (Philips Corp., The Netherlands) to apply known signals to the image display device and then comparing the photometric measurements of the display to values expected for such known signals. Signal generators provide electrical video signals of known characteristics to image display devices for the purpose of testing or calibration. Alternately, known signals, such as straight lines and squares, can be fed into the image pick up providing signal to the monitor by placing the image in front of the image pick up. Such known signals are representative of reference standards, which are standards used having known characteristics providing one approach to calibrating systems can measuring background.

Measurement of transmission of light through the optical paths of an endoscope can be accomplished using the illumination unit and the measurement unit of the photometric measurement module. The output of the illumination unit is first measured by connecting the calibration adapters between the illumination source and the measurement unit and measuring the lamp output, similar to the measurement of an endoscopy source discussed above. Then an optical aperture of the sample device is connected to the input port of the measurement integrating sphere and the corresponding, complement optical aperture of the sample device is connected to the output port of the illumination integrating sphere. The two measurements are tested and evaluated by the software in a manner similar to above. Evaluation of the transmission characteristics comprises comparing the emission of the light source to the reference emission value and then comparing the transmission of the endoscopy device to the reference transmission for the endoscopy device.

The structural element measurement module measures physical characteristics of the mechanical, pneumatic and fluidic systems of an endoscope. The module makes measurements to evaluate the endoscope articulation, integrity of the endoscope lumens and the ability of the endoscopy system to provide insufflation, irrigation and suction. To evaluate each of these properties the module is typically equipped with sensors to measure range of movement, flow, pressure and volume delivery. Each of the sensor blocks is equipped with a standardized port that will accept the various adapters for connection to the endoscope. The sensor blocks can be used alone to evaluate the structural systems. In addition to the sensor blocks there are air, fluid and vacuum sources and reservoirs to provide controlled output for evaluating performance of endoscopy devices that transfer these services to and from tissues or other devices. Typical adapters include an endoscope/light-source connector adapter, endoscope suction port adapter, endoscope biopsy port adapter, endoscope irrigation port adapter, endoscope tip adapter light source adapter and an endoscope tip adapter.

Fluid, vacuum and air delivery through an endoscope can be measured by using the air, fluid and vacuum sources and reservoirs to provide controlled input and then measuring the results. The desired adapters are connected to the input and output ports of the sample device, then the flow and pressure sensors of the measurement module make a series of measurements while the services are applied and the measurement module simulates a range of flow and back-pressure conditions. By applying various sequences of dynamic and static input and output conditions and measuring the flow and pressure characteristics at the input and output ports the system generates a data set that can be analyzed for performance characteristics.

Measurement of the effect of fluid, vacuum and air activities on the optical activities of an endoscope can be accomplished by connecting the endoscope to the photometric measurement module and evaluating image quality or photometric performance characteristics while simultaneously using the structural element measurement module to measure structural performance characteristics of the endoscope. For example, the flow and pressure sensors of the structural element measurement module can make a series of measurements under various flow and back-pressure conditions while the optical system of the endoscope is also operated and the image quality or photometric measurement module makes its measurements.

To do the measurement, for example, software acquires measurement data. An auto-ranging algorithm evaluates the data to determine if the measurement is of sufficient signal strength and then adjusts measurement integration time until the signal is suitable or an error code is generated. The service source is then turned off and the user initiates a background measurement with the same integration time as for the service measurement; as with other embodiments of the invention, the background can be obtained first if desired. The background measurement is subtracted from the service measurement, preferably in view of any applicable calibration factors.

The analysis software compares characteristics of the measurement data to predetermined characteristics that define an acceptable quality measurement using similar criteria as described elsewhere herein. If the measurement is acceptable, the analysis software then compares the values and provides analysis, tracking and reports, also as discussed elsewhere herein.

The image quality measurement module comprises imaging targets and test patterns, a high-resolution image sensor for evaluating the quality of optical images, and an analog and/or digital video signal acquisition system. The module, in conjunction with the image evaluation software, measures the image quality of optical endoscopes, as well as the image quality characteristics of video endoscopes and endoscopic video camera systems. Some of these characteristics include image size, spatial distortion, contrast, brightness, image resolution, focus and modulation transfer function. Brightness can be defined as the relative number of photons emitted or reflected from a surface. Contrast is the difference in brightness between one object or object area and another. Focus is the point at which collimated light, refracted when passing through a lens, converges. With reference to imaging, it is the point at which a real image after passing through a lens exhibits a maximum modulation transfer function. This point is also known as a conjugate image plane of the sample, which in this case the sample itself may be an image.

Optical endoscopes employ an optical image guide to transfer a tissue image to an endoscope ocular. Video endoscopes are endoscopes that do not employ an optical image guide to transfer a tissue image to an endoscope ocular, but instead employ an image sensor located distally on the endoscope and proximal to the tissue. Instead of employing an optical relay system to transfer the image to the viewer or camera, the image is focused by the objective lens system on to the image sensor and then transduced and transferred electronically to the image processing and/or display system.

The image quality measurement module measures and tracks difficulties such as image bundle fiber defects or image sensor pixel defects. Image quality performance characteristics include image size, spatial distortion, modulation transfer function (MTF), intra-scene dynamic range, and illumination field characteristics. For video systems, additional measurements can include black level, white level, synchronization signal characteristics, synchronization signal stability over time and ranges of image brightness and gain settings.

The image sensor and image target blocks are typically equipped with a standardized port that will accept various accessory devices. These accessories allow coupling of various manufacturers products and devices to be tested to the core module. Typical adapters to connect the image quality measurement module to the sample device includes endoscope/light-source connector adapters, endoscope tip adapters, endoscope ocular adapter, and video and control signal connectors.

To measure the imaging quality of optical endoscopes, for example, the ocular adapter of the endoscope is connected to the input port of the image measurement unit and the endoscope tip adapter is inserted into the endoscope image quality target adapter and positioned to view the image quality target. The image quality target presents an image of known characteristics. The image quality target comprises various combinations of lines and areas of various colors and intensities. The image quality target may be back illuminated, or may be illuminated by the endoscope light source, or otherwise illuminated.

The image sensor of the measurement module then makes a series of measurements of the relayed image of the image quality target. Preferably, the image sensor comprises a linearly arrayed sensing element, such as a line scan CCD detector or a linear diode array. One example of a one-dimensional high-resolution linear CCD array, is a 1×2000 pixel CCD sensor produced by Sony Corporation. The linearly arrayed sensing element can have more than one line, for example 3 lines, or the image sensor can be non-linear and be a two-dimensional array. In further embodiments of the invention the one-dimensional image sensor may be scanned by being moved (e.g., translated or rotated) across a conjugate image plane of the sample (or by moving the conjugate image plane across the one-dimensional, array) and acquiring a sequence of linear measurements which can be reconstructed by software to generate a two dimensional image.

To do the measurement, for example, software acquires measurement data. An auto-ranging algorithm evaluates the data to determine if the measurement is of sufficient signal strength and then adjusts measurement integration time until the signal is suitable or an error code is generated. The image target illumination is then turned off and the user initiates a background measurement with the same integration time as for the image measurement. The measurement algorithm subtracts the background measurement from the image measurement and applies any calibration factors. The measurement data is then stored in an electronic database for analysis.

Measurement of video endoscopes is similar to the above, except that the image sensor does not need to create an electronic image signal to be evaluated, although it can be used if desired. Instead the electronic video signal is acquired directly from the image sensor by an electronic image capture device known as an imaging board (National Instruments Ltd., Houston, Tex.), which are usually connected to or installed in a computer. The imaging board converts the analog or digital electronic signal to image measurement data.

The image quality analysis software compares characteristics of the measurement data to predetermined characteristics that define an acceptable quality measurement, similar to the procedures described above. If the measurement is considered acceptable, the analysis software compares the values of characteristic features of the measurement data to threshold values of features that identify acceptable performance levels for the device being measured. Such features may include spatial distortion of the relative orientation of features of the target when it is imaged, loss of resolution or loss of focus. These values are presented to the user via the system controller display and are recorded electronically in the device database. Any failures to meet acceptable performance levels for the device being measured are identified and reported to the user.

Figure 12:
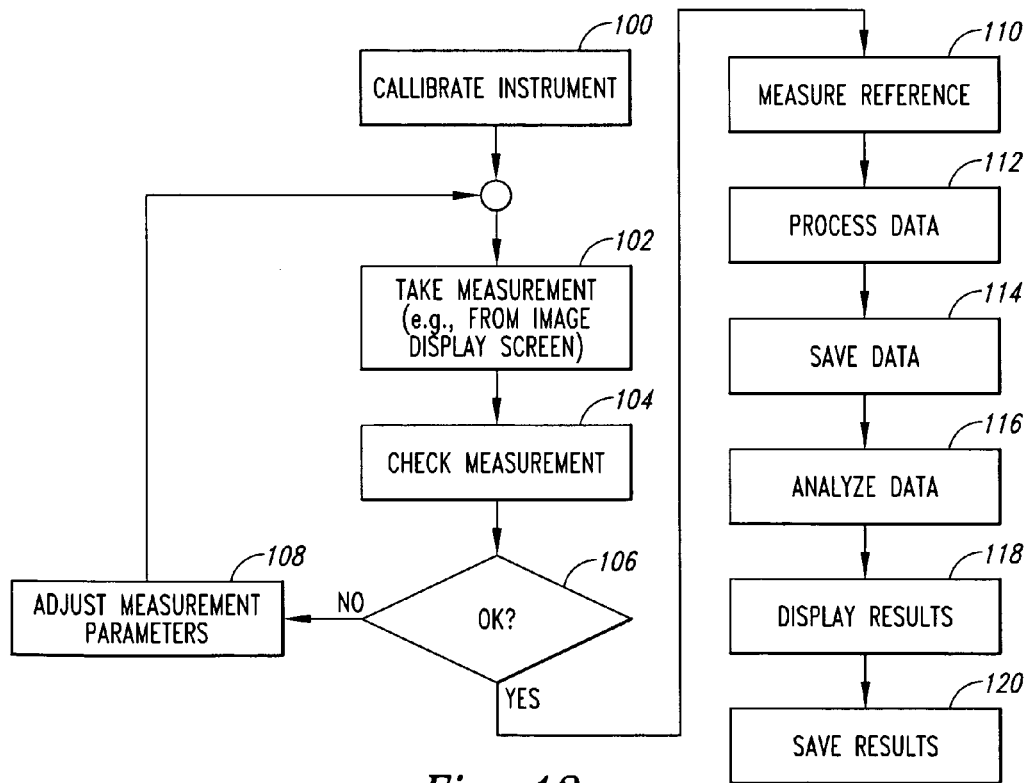
FIG. 12 is a flow chart depicting a typical data acquisition sequence.

The actions of controller and computer-implemented programming, and certain methods of the present invention, are depicted in flow chart form in FIG. 12. Briefly, and using photometric quality measurement as an example, first the instrument is calibrated 100. This can include calibrating the measurement module, the illumination module, or any other part of the system for which calibration can be useful, and can comprise calibration using a reference standard to provide calibration correction factors, and application of the calibration correction factors to the collected data to provide a corrected data set.

Next, a sample measurement, such as the acquisition of spectral data, of the sample endoscope is taken 102. This can be controlled by the controller or by a human operator, or a combination of the two. The data are then checked 104 to be sure that they are within appropriate limits, such as sufficient signal strength and detector saturation. In decision step 106, if the signal is acceptable, or okay, then the system proceeds to measure a reference standard, background or dark spectrum 110. Measurements of the reference standard are acquired and can stored as a background signal data set. If the measurement 104 is not adequate, then the measurement parameters are adjusted 108, and the method is returned to taking a measurement 102.

Once the reference standard is measured 110, the measurement signal data set representing raw data obtained from the sample device is then processed 112 by subtracting the reference standard measurement (e.g., background) from the measurement signal data set, or sample measurement to generate a background corrected measurement data set. The calibration correction factors can also be applied to the background corrected measurement data set to generate a calibrated measurement data set, or to the raw data to provided a corrected measurement data set.

The processed data is preferably saved or recorded 114, then analyzed 116. The analysis can include determining if the background corrected measurement data set is of acceptable quality to provide an acceptable background measurement data set, providing an indicator to the operator if the background corrected measurement data set is not of acceptable quality. The analysis can also include determining a performance characteristic for at least one of the photometric characteristics, the image quality characteristics and the structural element characteristics based on the background corrected measurement data set with the calibration measurement data set, preferably all of such characteristics.

The results are then displayed 118, which can be on a screen, in a print out, or otherwise such that the user can assess the results. The results are also saved 120. The saved results, as well as the saved data, can be used to track performance trends over time of at least one of the photometric characteristics, image quality characteristics and structural element characteristics.

From the foregoing, it will be appreciated that, although specific embodiments of the invention have been described herein for purposes of illustration, various modifications may be made without deviating from the spirit and scope of the invention. Accordingly, the invention includes all permutations and combinations of the subject matter set forth herein and is not limited except as by the appended claims.

The invention claimed is:

1. A photometric measurement system comprising an integrating sphere optically connected to receive light transmitted through a measurement probe sized and shaped to receive light from an image display screen, the integrating sphere further optically connected to transmit light to a photometric measurement device comprising a spectrometer comprising a wavelength dispersive element, wherein the photometric measurement system is operably connected to a controller containing computer-implemented programming that responds to a set of operator input instructions to control the data acquisition and analyses of the photometric measurement system and that controls measurement of the image display screen, wherein the image display screen is operably connectable to an endoscope to display an image transmitted from the endoscope.

2. The photometric measurement system of claim 1 wherein the computer-implemented programming additionally analyzes the data obtained from the photometric measurement module to determine if the data comprises an acceptable signal level and if not then adjusts data acquisition until the acceptable signal level is obtained.

3. The photometric measurement system of claim 2 wherein the computer-implemented programming further provides an indicator to the operator if the acceptable signal level is not obtained.

4. The photometric measurement system of claim 1 wherein the image display screen is operably connectable to a signal generator able to generate a plurality of test signals on the image display screen.

5. A photometric measurement system comprising an integrating sphere optically connected to receive light transmitted through a measurement probe sized and shaped to receive light from an image display screen, the integrating sphere further optically connected to transmit light to a photometric measurement device comprising a spectrometer comprising a wavelength dispersive element, wherein the photometric measurement system is operably connected to a controller containing computer-implemented programming that responds to a set of operator input instructions to control the data acquisition and analyses of the photometric measurement system and that controls measurement of the image display screen, wherein the image display screen is operably connectable to a signal generator able to generate a plurality of test signals on the image display screen.

6. The photometric measurement system of claim 5 wherein the computer-implemented programming additionally provides for calibration of a response of a photometric measurement module using a reference standard to provide calibration correction factors, and application of the calibration correction factors to the data collected by the photometric measurement module to provide a corrected data set.

7. The photometric measurement system of claim 6 wherein the computer-implemented programming additionally provides for acquisition and storage of at least one of a dark spectrum signal data and a background signal data set; acquisition and storage of a measurement signal data set; and, subtraction of the background signal data set from the measurement signal data set to generate a background corrected measurement data set.

8. The photometric measurement system of claim 7 wherein the computer-implemented programming additionally applies the calibration correction factors to the background corrected measurement data set to generate a calibrated measurement data set.

9. The photometric measurement system of claim 8 wherein the computer-implemented programming additionally:
analyzes the calibrated measurement data set to determine if the calibrated measurement data set is of acceptable quality to provide an acceptable calibrated measurement data set and provides an indicator to the operator if the calibrated measurement data set is not of acceptable quality;
analyzes the acceptable calibrated measurement data set and provides an indication to a user of a performance characteristic for the photometric characteristics.

10. The photometric measurement system of claim 9 wherein the computer-implemented programming additionally determines whether the performance characteristic is within an acceptable range.

11. The photometric measurement system of claim 10 wherein the computer-implemented programming additionally records the performance characteristic in a computer-readable memory to provide a recorded measurement data set.

12. The photometric measurement system of claim 11 wherein the computer-implemented programming additionally compares and analyzes at least one performance characteristic from a recorded measurement data set and at least one additional performance characteristic from a different time for at least one temporal trend.

13. The photometric measurement system of claim 12 wherein the computer-implemented programming additionally provides an indicator of the temporal trend.

* * * * *